(12) United States Patent
Kendig et al.

(10) Patent No.: US 8,016,987 B2
(45) Date of Patent: *Sep. 13, 2011

(54) EVALUATION OF THE CORROSION INHIBITING ACTIVITY OF A COATING

(75) Inventors: Martin W. Kendig, Thousand Oaks, CA (US); Melitta M. Hon, Woodland Hills, CA (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 446 days.

This patent is subject to a terminal disclaimer.

(21) Appl. No.: 12/218,148

(22) Filed: Jul. 11, 2008

(65) Prior Publication Data

US 2009/0050478 A1    Feb. 26, 2009

Related U.S. Application Data

(63) Continuation of application No. 10/690,787, filed on Oct. 21, 2003, now Pat. No. 7,422,678.

(51) Int. Cl.
*G01N 27/403* (2006.01)
(52) U.S. Cl. .................................................. 204/404
(58) Field of Classification Search ........... 205/775.5, 205/776, 776.5, 777; 204/404
See application file for complete search history.

(56) References Cited

U.S. PATENT DOCUMENTS

| 4,871,024 A * | 10/1989 | Cizek ............................ 166/307 |
| 6,365,034 B1 | 4/2002 | Spellane .................... 205/775.5 |
| 6,621,263 B2 | 9/2003 | Al-Janabi et al. ............. 324/200 |
| 7,422,678 B2 * | 9/2008 | Kendig et al. .............. 205/775.5 |

FOREIGN PATENT DOCUMENTS

| GB | 2054865 A | 2/1981 |
| JP | 868774 | 3/1996 |

OTHER PUBLICATIONS

Sekine, Isao, "Recent Evaluation of Corrosion Protective Paint Films by Electrochemical Methods", Progress in Organic Coatings 31, (1997), pp. 73-80.

* cited by examiner

*Primary Examiner* — Alex Noguerola
(74) *Attorney, Agent, or Firm* — Koppel, Patrick, Heybl & Philpott

(57) ABSTRACT

The corrosion inhibiting activity of a coating is determined from the effect of corrosion inhibiting species released by the coating on the oxygen reduction current for a cathode placed very close to the coating. A rotating disk electrode or pumped solution flow is used to sweep the corrosion inhibiting species from the coating surface to the cathode. The oxygen reduction current is measured under conditions of oxygen diffusion control.

8 Claims, 4 Drawing Sheets

EVALUATION OF THE CORROSION INHIBITING ACTIVITY OF A COATING

This application is a continuation of and claims the benefit of U.S. application Ser. No. 10/690,787 to Kendig et al. filed on Oct. 21, 2003, now U.S. Pat. No. 7,422,678.

BACKGROUND OF THE INVENTION

1. Field of the Invention

This invention is concerned with corrosion inhibition, and in particular with detection of corrosion inhibiting species released from a coating.

2. Description of the Related Art

Corrosion of a metal or alloy generally involves oxidation of metal atoms (M), which may dissolve in a liquid, or form a solid compound such as a metallic oxide. The driving force for such metallic corrosion is typically oxygen reduction, which consumes the electrons generated during oxidation of the metal atoms. The metal oxidation reaction and the oxygen reduction reaction form an electrochemical couple defined by the general half reactions:

$$M \rightarrow M^{x+} + xe^- \quad (1)$$

and $$O_2 + 2H_2O + 4e^- \rightarrow 4OH^- \text{ (in alkaline solutions)} \quad (2)$$

or $$O_2 + 4H^+ + 4e^- \rightarrow 2H_2O \text{ (in acidic solutions)} \quad (3)$$

For this couple, the anodic reaction is metal oxidation and the cathodic reaction is oxygen reduction. Although not shown for these overall half reactions, oxygen reduction generally proceeds via a peroxide intermediate, which may be the reaction end product under some conditions.

The oxygen reduction reaction, which typically provides the driving force for metallic corrosion, is sustained only in the presence of a catalyst. Oxygen reduction tends to be catalyzed by more noble metals, e.g., osmium, ruthenium, iridium, rhodium, platinum, palladium, gold, silver and copper. Less noble metals tend to react rapidly with oxygen to form a relatively thick surface oxide layer that inhibits further oxygen reduction. Oxygen reduction is also catalyzed by some forms of carbon and some carbon compounds.

An impurity or a constituent added to impart desirable physical or chemical properties to an alloy may serve as an oxygen reduction catalyst, reducing the corrosion resistance of the alloy. For example, high-strength aluminum alloys often contain copper, which tends to segregate at aluminum grain boundaries and form catalytic sites at the alloy surface. In the presence of liquid water or an aqueous solution, the copper sites may serve as cathodes at which oxygen is reduced so that electrons are withdrawn from the alloy, causing aluminum metal to be electrochemically oxidized to aluminum ions.

Corrosion inhibitors, such as hexavalent chromium ions, are often added to paints, primers and other coatings to suppress corrosion of the underlying metal. It is known in the art that such corrosion inhibitors typically function by adsorbing or reacting at catalytic cathode sites so that the oxygen reduction reaction is suppressed [G. O. Ilevbare and J. R. Scully, J. Electrochem. Soc. 148 (5), B196 (2001); and M. Kendig and S. Jeanjaquet, J. Electrochem. Soc. 149 (2), B47 (2002)]. Corrosion tends to be more effectively suppressed if the inhibitor is released from the coating slowly, or as needed to inhibit corrosion at a damaged area in the coating. When the inhibitor becomes depleted in the coating, the extent of corrosion protection provided by the coating is diminished. Furthermore, the effectiveness of a corrosion inhibitor typically depends on the type of coating in which the inhibitor is included and may be degraded by variations in the coating constituents, formulation and application process.

A rapid and effective method for evaluating the corrosion inhibiting activity of a coating is needed to efficiently identify effective combinations of corrosion inhibitors, coatings and application processes. This need is particularly important since the widely used hexavalent chromium inhibitor has been found to be environmentally unacceptable. Such a coating evaluation method could also be used for quality control to ensure that the coating application process consistently provides coatings with high corrosion inhibiting activity. There is also an important need for a rapid, portable, inexpensive and non-destructive means for periodically evaluating the corrosion inhibiting activity of coatings during use to determine when coating renewal or other preventative maintenance is needed. Reliable information concerning the corrosion inhibiting activity of a coating could be used to save time, effort and expense by deferring coating renewal until needed while avoiding corrosion damage to the substrate that might require more costly repairs or result in substrate failure. However, prior art methods for evaluating corrosion inhibiting coatings are inadequate.

The effectiveness of a coating in suppressing corrosion of a substrate is typically determined by standard salt spray or salt fog tests (ASTM B117), in which a coated substrate is exposed to a corrosive environment and subsequently examined for signs of substrate corrosion. The corrosive environment typically includes air and a saline solution (salt fog may also include other corrosive species, such as $SO_2$ gas). A coating defect may be intentionally introduced (by scribing, for example) to assess the effectiveness of damaged or defective coatings for inhibiting corrosion of the substrate. Typical evaluation criteria are the number of coating pores or defects discolored by corrosion products, and the degree of discoloration. Such evaluations are subjective since the pore/defect size and the extent and the nature of the discoloration may vary widely. These tests also involve bulky aging chambers and long exposure times (typically 168 to 336 hours for anodized coatings and conversion coatings, and 1000 to 2000 hours for paint primers), and are costly to perform. Furthermore, the harsh test conditions employed may not yield results that predict the performance of the coating in actual use. In addition, salt spray and salt fog tests are destructive so that they cannot be used for periodic evaluation of a coating in service to determine the need for renewal of the coating or other preventative maintenance.

Electrochemical methods, such as electrochemical impedance spectroscopy (EIS), are often used to measure corrosion rates of metals and alloys, with and without corrosion protective coatings. These methods involve direct measurement of the current associated with the substrate corrosion process and are thus insensitive to the corrosion inhibiting activity of the coating until significant substrate corrosion has already begun. Consequently, electrochemical methods of the prior art cannot be used to evaluate the corrosion inhibiting activity of a coating prior to depletion of the inhibitor. In addition, corrosion rate measurements are substantially insensitive to the small amounts of corrosion inhibitor typically released from a corrosion protective coating.

SUMMARY OF THE INVENTION

This invention provides a method and an apparatus for evaluating the corrosion inhibiting activity of a coating via detection of a corrosion inhibiting species released by the coating. A cathode comprising an oxygen reduction catalyst is placed in close proximity to the coating. The electrolytic solution is caused to flow laminarly over the surfaces of the coating and the cathode such that at least some of any corrosion inhibiting species released by the coating are brought into physical contact with the cathode surface. Laminar flow over the two surfaces may be provided via a rotating disk electrode or pumped solution flow. A potential is applied between the cathode and an anode in the electrolytic solution such that oxygen in the electrolytic solution is reduced at the cathode producing an oxygen reduction current. The extent to which the oxygen reduction current is reduced by the corrosion inhibiting species released by the coating is a measure of the corrosion inhibiting activity of the coating. More consistent results may be provided by measuring the oxygen reduction current under oxygen diffusion limited conditions.

The method of the present invention permits rapid, inexpensive and non-destructive evaluation of the corrosion inhibiting activity of a coating. Some embodiments of the apparatus of the present invention are sufficiently portable to be used for evaluation of coatings in the field. The invention is useful for identifying effective combinations of corrosion inhibitors, coatings and application processes, and for quality control to ensure that a coating application process consistently provides coatings with high corrosion inhibiting activity. The invention is also useful for periodic monitoring of corrosion inhibiting coatings during use to determine when coating renewal or other preventative maintenance is needed. Thus, the invention may be used to reduce costs by deferring coating renewal until needed while avoiding corrosion damage to the substrate that might require costly repairs or result in structural failure of the substrate.

Further features and advantages of the invention will be apparent to those skilled in the art from the following detailed description, taken together with the accompanying drawings.

BRIEF DESCRIPTION OF THE DRAWINGS

FIGS. 1 and 2 are not to scale and some features have been enlarged for better depiction.

DETAILED DESCRIPTION OF THE INVENTION

Figure 1:
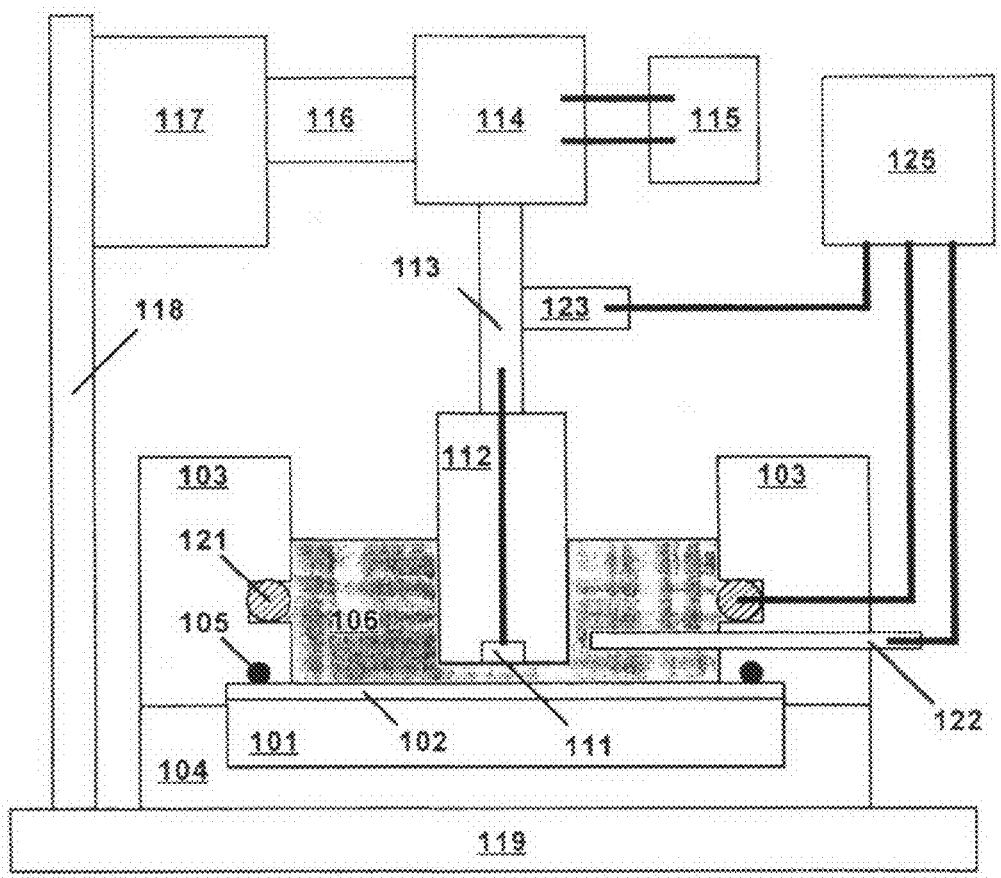
FIG. 1 is a schematic representation of an apparatus for evaluating the corrosion inhibiting activity of a coating using a rotating disk cathode.

Technical terms used in this document are generally known to those skilled in the art. Electrochemical measurements are usually performed in a "cell" containing an electrolytic solution (or "electrolyte") and at least two electrodes. Electroanalytical measurements are typically made by applying a voltage between a "working electrode" (also termed "indicator electrode") and a "counter electrode" and measuring the resulting current and the potential of the working electrode relative to a "reference electrode". The term "electrode potential", or simply "potential", refers to the voltage occurring across a single electrode-electrolyte interface.

A "potentiostat" is an electronic device for controlling the potential of a working electrode by passing current between the working electrode and the counter electrode so as to drive the working electrode to a desired potential relative to the reference electrode. Use of a potentiostat avoids passing appreciable current through the reference electrode, which might change its potential. Errors in electrode potential measurements associated with the resistive voltage losses in the electrolyte may be minimized by placing the reference electrode in a separate compartment connected to the cell solution via a Luggin capillary whose tip is close to the working electrode surface. A "voltammogram" is a plot of current or current density (on the y-axis) versus the working electrode potential (on the x-axis) typically obtained by sweeping the working electrode potential linearly with time between predetermined potential limits. The symbol "$\underline{M}$" means molar concentration.

The "rotating disk electrode" configuration is widely used for electrochemical measurements to provide laminar solution flow and well-defined hydrodynamic conditions at the working electrode surface. A typical rotating disk electrode is comprised of a flat metal disk (typically 2-6 mm diameter), with an electrical contact wire on the backside, embedded flush with one end of an insulating cylinder (typically 10-20 mm diameter). The insulating material is usually a halocarbon polymer (Teflon® or Kel-F®). The disk electrode may be press fitted into the insulating material but is preferably embedded in Kel-F® by hot pressing, which seals the sides of the electrode and prevents electrolyte leakage. The rotating disk electrode is typically attached to a rotator (via a threaded screw) and immersed vertically in an electrolytic solution. Rotation of the rotating disk electrode at a predetermined rate provides laminar flow of the solution over the electrode surface (spiraling outward from the center of the disk) and a constant diffusion layer thickness. Solution is drawn upward toward the center of the disk electrode to replenish that thrown off the electrode by centrifugal force. The rotation rate range over which laminar flow is provided by a rotating disk electrode depends on the electrode and cell geometries, the solution kinematic viscosity, and the depth to which the electrode is immersed in the solution. The theoretical upper limit for laminar flow at a rotating disk electrode is about 10,000 rpm. Rotation rates below about 100 rpm tend to yield variable diffusion limited currents with excessive noise.

According to the present invention, the corrosion inhibiting activity of a coating is evaluated by detecting corrosion inhibiting species released from the coating into an electrolytic solution under well-defined hydrodynamic conditions. The corrosion inhibiting species are detected from the decrease produced in the oxygen reduction current at a catalytic cathode positioned very close to the coating surface. Well-defined hydrodynamic conditions involving laminar solution flow are provided by use of a rotating disc cathode or forced solution flow. The invention may be used to evaluate coatings that release one or multiple corrosion inhibiting species.

FIG. 1 depicts an apparatus according to the present invention for evaluating the corrosion inhibiting activity of a coating using a rotating disk cathode. For this description, the coated substrate is assumed to be circular but substrates of other geometric shapes could be evaluated using analogous apparati. Substrate 101 with coating 102 is clamped, using a series of screws (not shown), between a top ring 103 and a bottom disk 104 made of an inert insulating material, polypropylene, Kel-F®, Teflon® or polyvinylchloride, for example. Polymer o-ring 105, which preferably fits in an o-ring groove in top ring 103 (not shown), forms a seal between coating 102 and top ring 103 so that electrolytic solution 106 is contained.

Rotating disk cathode 111 embedded in one end of insulating cylinder 112 is connected (physically and electrically) to metallic motor shaft 113 of motor 114 whose speed, usually given in revolutions per minute (rpm), is controlled by motor controller 115. Rotating disk cathode 111 may alternatively be connected to a separate shaft driven by a motor via a pulley or gear arrangement (not shown). Motor 114 is attached via bracket 116 to a means 117 for precisely controlling the location of rotating disk electrode 111 relative to coating 102. Means 117 may be a linear motor or micrometer positioner, for example, which is firmly attached to base plate 119 via bracket 118 so that the spacing between coating 102 and cathode 111 can be consistently reproduced. Those skilled in the art will readily envision a variety of means for providing a reproducible spacing between coating 102 and cathode 111, including those based on the use of mechanical stops or spacers.

Anode 121 is preferably a circular wire or rod that fits within a groove in top ring 103. Anode 121 is preferably maintained at a substantial distance (more than 1.0 cm) from cathode 111 so that species generated electrochemically at the anode are substantially diluted in solution 106 or dissipated by equilibration with air before they reach the cathode and interfere with the oxygen reduction current measurement. A wide variety of anode materials may be used but an inert metal (platinum or stainless steel, for example) is preferred so that the anodic product is oxygen, which dissipates in air. The anode may also be placed in a separate compartment (not shown) separated by a frit or membrane, for example, so that anodic reaction products are substantially prevented from reaching the cathode.

As shown in FIG. 1, measurements of the oxygen reduction current at cathode 111 are preferably made using a reference electrode 122 and a potentiostat 125. Cathode 111, anode 121 and reference electrode 122 are connected to potentiostat 125 via wires (indicated by the thick lines in FIG. 1). Cathode 111 is electrically connected to metallic rotating motor shaft 113, which is electrically connected to potentiostat 125 via sliding electrical contact 123, which may be a contact brush or a mercury contact, for example. Reference electrode 122 may be inserted directly in solution 106 (as shown) or be connected to solution 106 via a Luggin capillary (not shown). The tip of reference electrode 122 or the Luggin capillary is preferably located near cathode 111 to minimize errors in the potential measurement associated with resistive voltage losses in the solution. This is not essential, however, especially if the oxygen reduction current is measured under oxygen diffusion control, for which small changes in electrode potential do not substantially affect the measured current. The invention may also be practiced without the use of a separate reference electrode by using an anode that is not substantially polarized by the currents passed at the cathode. Polarization of the anode may be minimized by using an anode area that is relatively large compared to that of the cathode. When the anode also serves as the reference electrode, a power supply may be used to apply a voltage between the cathode and the anode.

For the apparatus of FIG. 1, the method of the present invention involves rotating the rotating disk cathode at a constant rate to produce laminar flow of solution 106 over the surfaces of cathode 111 and coating 102, and applying a potential to cathode 111 relative to reference electrode 122 such that diffusion limited oxygen reduction occurs at cathode 111. Corrosion inhibiting species released from the coating are transported to the cathode surface and suppress the oxygen reduction current.

Figure 2:
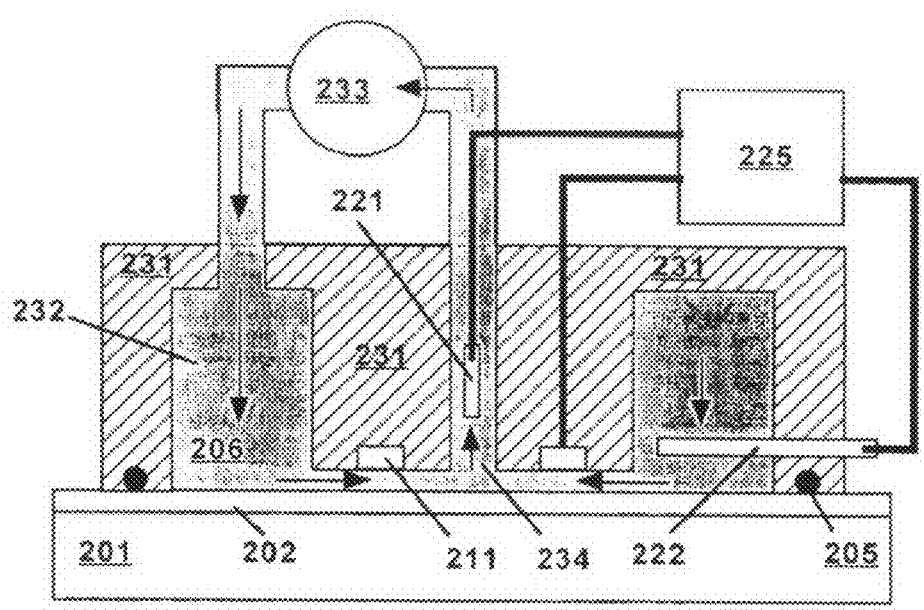
FIG. 2 is a schematic representation of an apparatus for evaluating the corrosion inhibiting activity of a coating using pumped solution flow between the coating and a stationary cathode.

FIG. 2 depicts an apparatus according to the present invention for evaluating the corrosion inhibiting activity of a coating using forced solution flow between the coating and a stationary cathode. For this embodiment, the cathode 211 is a metal ring embedded, preferably via hot pressing, in a cylindrical plastic housing 231 having a ring-shaped cavity 232 for containing the electrolytic solution 206. When housing 231 is held against coating 202 on substrate 201, o-ring 205 in a groove (not shown) in housing 231, forms a seal between housing 231 and coating 202. By means of a valve system (not shown) and pump 233, solution 206 is pumped from a reservoir (not shown) into cavity 232, and is then circulated, as indicated by the arrows in FIG. 2. During circulation, solution 206 passes laminarly through a gap between cathode 211 and coating 202, and is returned to pump 233 via a hole 234 in housing 231 at the center of cathode 211. Solution 206 may also be circulated in the opposite direction. Corrosion inhibiting species released by coating 202 are detected at cathode 211 from the reduction in the diffusion-limited oxygen reduction current measured via anode 221 (located in hole 234), reference electrode 222, and potentiostat 225. Cathode ring 211 is preferably located sufficiently far from corners in housing 231 to avoid turbulence at the cathode surface. The dimensions of cathode ring 211 are preferably chosen such that the flowing solution contacts coating 202 for a substantial time immediately before flowing over the surface of cathode 211. A long contact time between solution 206 and coating 202 tends to improve the sensitivity of the oxygen reduction current to corrosion inhibiting species released from coating 202. A reproducible distance between cathode 211 and coating 202 is provided by compressing o-ring 205 so that housing 231 contacts coating 202. This type of apparatus may be used to non-destructively evaluate the corrosion inhibiting activity of coatings during use, and could be designed for use with vertical surfaces. Additional reservoirs and an appropriate valving system could be provided to enable circulation of various liquids, for example, copper plating solution and rinse water for providing a fresh copper cathode surface. A wide variety of alternative apparati based on forced solution flow may be used to practice the invention.

The present invention may be used to evaluate the corrosion inhibiting activity of any corrosion protective coating that functions by releasing a corrosion inhibitor to suppress the oxygen reduction reaction. Such coatings include paints, primers, overcoats, conversion coatings, anodized coatings, and conducting polymer coatings (polyaniline, polythiophene and polypyrrole, for example) that are charged with corrosion inhibitors. For evaluation of conducting polymer coatings, a voltage may be applied to the coating to stimulate release the corrosion inhibiting anion.

The method for evaluating the corrosion inhibiting activity of a coating according to the present invention comprises the steps of:

(1) providing a cathode comprising an oxygen reduction catalyst;

(2) placing the cathode, an anode and the coating in electrical contact with an electrolytic solution;

(3) positioning the cathode at a predetermined distance from the coating;

(4) causing the electrolytic solution to flow laminarly between the coating and the cathode;

(5) applying a voltage between the cathode and the anode such that oxygen in the electrolytic solution is reduced at the cathode and an oxygen reduction current flows through the cathode;

(6) measuring the oxygen reduction current flowing through the cathode under reproducible and constant hydrodynamic conditions; and (7) comparing the oxygen reduction current measured in Step (6) with the oxygen reduction current measured under equivalent conditions but in the absence of substantial effects of corrosion inhibiting species. Such a baseline measurement may be made in the absence of a coating, or in the absence of corrosion inhibiting species in the coating. The baseline measurement may also be made using a large distance between the coating and the cathode such that corrosion inhibiting species released by the coating have substantially no effect on the oxygen reduction current at the anode.

The order in which these steps are performed may vary.

The concentration of oxygen in the electrolytic solution is typically defined by equilibration with ambient air but this parameter could be varied by utilizing a sealed cell and equilibrating the solution with a gas containing a different concentration of oxygen. Use of a different solution oxygen content might provide improved sensitivity or reproducibility for evaluation of some coatings.

Suitable oxygen reduction catalysts include osmium, ruthenium, iridium, rhodium, platinum, palladium, gold, silver, copper, carbon, and alloys thereof. Preferred oxygen reduction catalysts are impurities or alloy constituents in the coating substrate that catalyze oxygen reduction during corrosion of the substrate. For example, copper is a preferred cathode material for evaluating coatings on high strength aluminum alloys containing copper.

A reproducible cathode surface state is needed to provide consistent measurements of oxygen reduction currents. Abrasive polishing or chemical etching may be used to provide a reproducible cathode surface. For a copper cathode, a preferred procedure is to electrodeposit copper on a cathode comprised of an inert metal (platinum, for example), and to electrochemically or chemically strip and re-deposit the copper before each coating evaluation. A preferred solution for electrodeposition of copper is copper pyrophosphate, which can be used without organic additives. Inert metal cathodes used as oxygen reduction catalyst may be conditioned by an anodic treatment in the oxygen evolution potential region to remove both organic and inorganic contaminants from the surface via oxidation.

A wide variety of electrolytic solutions comprising salts of relative stable ions may be used for evaluations according to the present invention. Suitable electrolytic solutions include the sodium or potassium cations with sulfate, perchlorate or halide anions, or mixtures thereof. The anode material is preferably an inert metal, platinum, for example, so that the anode reaction is oxygen evolution.

For maximum sensitivity to corrosion inhibitor released by the coating, the distance between the cathode and the coating should be small, but not so small as to cause deviations from laminar solution flow (turbulence), which would produce erratic oxygen reduction currents. Higher rates of cathode rotation or solution flow increase sensitivity to corrosion inhibiting species but may produce solution turbulence, especially for small distances between the cathode and the coating. Thus, the optimum distance between the cathode and the coating depends on the cathode rotation rate or the solution flow rate, in addition to the cell and electrode geometries. Suitable distances between the cathode and the coating are generally less than 1.0 mm. For a 4.2-mm diameter rotating disk electrode embedded in a 13-mm diameter insulating cylinder and rotated at 2000 rpm, good sensitivity to released corrosion inhibitor is attained with a 125 μm spacing between the cathode and the coating. The cathode and coating surfaces are typically parallel but alternative configurations may be used.

Laminar flow between the coating and the cathode may be provided by a rotating disk electrode or solution flow induced by pumping or other means (gravity flow, for example). Steady solution flow is preferred since pulsating flow would produce fluctuations in the diffusion-limited oxygen reduction current, and may induce turbulent flow.

The voltage applied between the cathode and the anode preferably produces oxygen reduction limited by diffusion of oxygen across the diffusion layer at the cathode surface. In this case, oxygen atoms are reduced as quickly as they reach the cathode surface so that the oxygen reduction current is substantially insensitive to the cathode potential so that errors or minor fluctuations in the applied voltage have minimum effect on the coating evaluation results. The voltage should be chosen so that electrochemical reactions other than oxygen reduction are substantially avoided. This can be best accomplished by exercising close control over the cathode potential via use of a reference electrode and a potentiostat.

Figure 3:
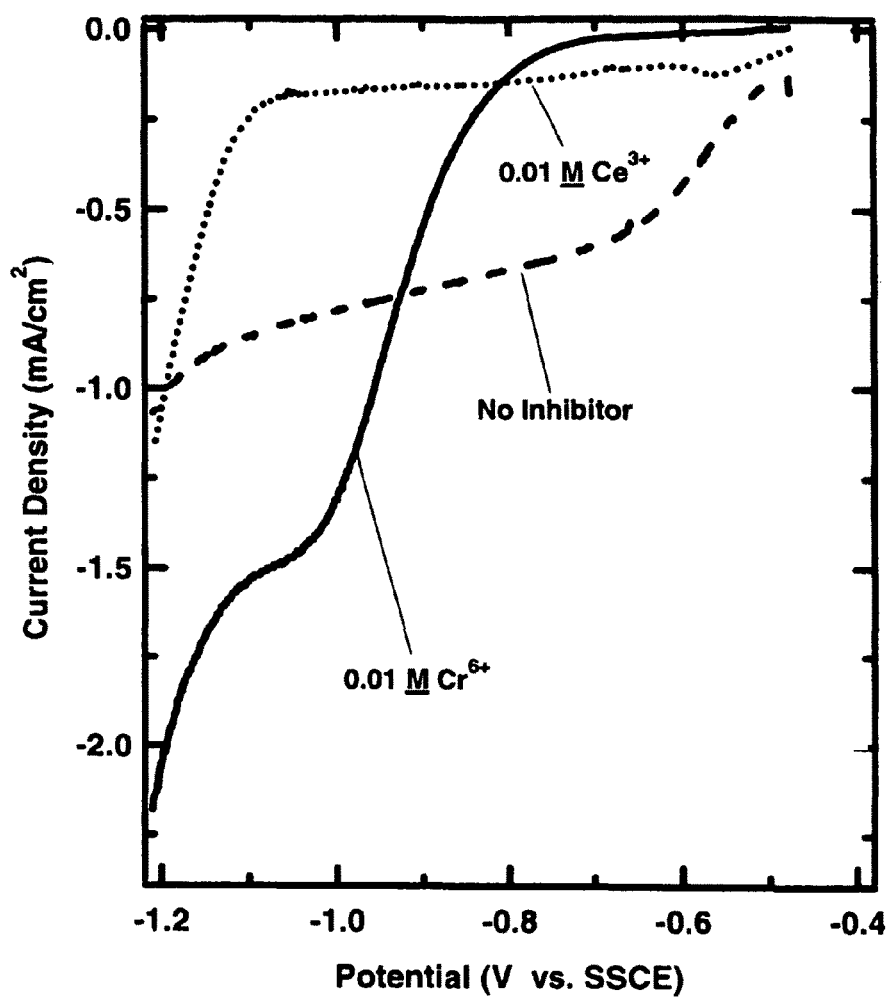
FIG. 3 shows linear sweep voltammograms (0.167 mV/s) for a copper rotating disk cathode (2000 rpm) in a 0.85 $\underline{M}$ NaCl solution, with and without 0.01 $\underline{M}$ $Cr^{6+}$ or $Ce^{3+}$ $\overline{ion}$ added.

Linear sweep voltammetry may be used to select a cathode voltage for which the current corresponds substantially to diffusion-limited oxygen reduction, as required for evaluations according to the present invention. FIG. 3 shows linear sweep voltammograms (0.167 mV/s) for a copper rotating disk cathode (2000 rpm) in a 0.85 M NaCl solution, with and without 0.01 M $Cr^{6+}$ or $Ce^{3+}$ ion added. In the absence of corrosion inhibiting species, the cathodic current increases at potentials more negative than about −0.5 V vs. SSCE (silver-silver chloride electrode) reaching an oxygen diffusion limited plateau extending from about −0.65 V to −1.1 V vs. SSCE. Addition of 0.01 M $Cr^{6+}$ or $Ce^{3+}$ ion is seen to greatly decrease the oxygen reduction. For the solution containing $Cr^{6+}$ ion, reduction of $Cr^{6+}$ produces a second current wave beginning at about −0.8 V vs. SSCE. In all cases, a cathodic current increase corresponding to hydrogen evolution is observed at about −1.1 V vs. SSCE. Based on these voltammograms, the current measured at a cathode potential of −0.7 V vs. SSCE corresponds only to diffusion-limited reduction of oxygen for both the $Cr^{6+}$ or $Ce^{3+}$ corrosion inhibiting species. Thus, this cathode potential is preferred for evaluations of corrosion inhibitors using a copper cathode in 0.85 M NaCl solution. Since the oxygen reduction onset potential and current-voltage behavior depend on the electrode material and the solution pH and composition, a different cathode potential may be preferred for other systems. A suitable cathode potential may be selected by reference to standard reduction potentials for the solution components but is preferably determined via voltammetric measurements.

Accurate evaluation of the corrosion inhibiting activity of a coating according to the present invention requires that the oxygen reduction current flowing through the cathode be measured under reproducible and constant hydrodynamic conditions. Thus, the rotation rate for a rotating disk electrode, or the solution flow rate for a stationary cathode, and the spacing between the cathode and the coating must be maintained substantially constant during measurement of the oxygen reduction current.

In some cases, it may be advantageous to electrochemically clean the surface of the cathode prior to measuring the oxygen reduction current. For example, contaminants may be removed from cathodes comprising a sufficiently noble metal by applying an anodic potential in the oxygen evolution region. For cathode materials that tend to form thicker surface oxide layers, copper, for example, a cathodic potential may be applied to reduce the oxide prior to measurement of the oxygen reduction current. Application of a cathode potential in the hydrogen evolution region ensures reduction of the surface oxide.

For evaluations of coatings containing some corrosion inhibiting species, the oxygen reduction current is preferably measured at a predetermined time after application of the cathode potential to allow steady-state conditions to be established. Oxygen reduction currents that decrease with time may result from slow accumulation of adsorbed corrosion inhibiting species at the cathode surface. A preferred time delay for the oxygen reduction current measurement is the time required for the oxygen reduction current to reach a substantially constant value, which may be determined for measurements of current as a function of time. A delay time of 1000 seconds or less is generally suitable.

The oxygen reduction current may be measured by any suitable means, an ammeter or current follower, for example. Modern potentiostats usually include a current follower that provides a direct readout of the current. Current may also be measured via the potential drop across a resistor in series with the cathode.

DESCRIPTION OF A PREFERRED EMBODIMENT

The efficacy of the present invention was demonstrated using an apparatus of the type shown in FIG. 1, with a 5.5-cm cell diameter. The cathode was a copper-plated platinum disk electrode (4.2 mm diameter) embedded in the end of a 13-mm diameter Teflon® cylinder and rotated at 2000 rpm (Pine Instrument AFMSRX analytical rotator). Prior to each coating evaluation, the Pt electrode was polished using fine abrasive (0.3 µm) and was electroplated at 30 mA/cm$^2$ with copper (2.0 µm thick) from a stirred copper pyrophosphate bath (55° C.) without organic additives [3.5 g/L $Cu^{2+}$ ion, 176.3 g/L $(P_2O_7)^{4-}$ ion, 2.1 g/L $NH_3$, and 7.4 g/L $NO_3^-$ ion] using a copper anode. After each coating evaluation, the copper deposit on the rotating disk was dissolved in 25% nitric acid solution. For coating evaluations, the anode was a Pt wire located in a groove around the inside circumference of the cell. The reference electrode was a 1.5-mm diameter commercial SSCE electrode (FlexiRef, World Precision Instruments) inserted through a hole at a 45° angle in the sidewall of the cell. The cathode was positioned 125 µm from the coating surface using a linear motor controller (Velmex Bislide MDL). Immediately prior to measurement of the oxygen reduction current at −0.7 V vs. SSCE, a cathode potential of −1.2 V was applied for 60 seconds to remove any oxide from the copper surface. For coating evaluations, the oxygen reduction current was measured after 1000 seconds.

Figure 4:
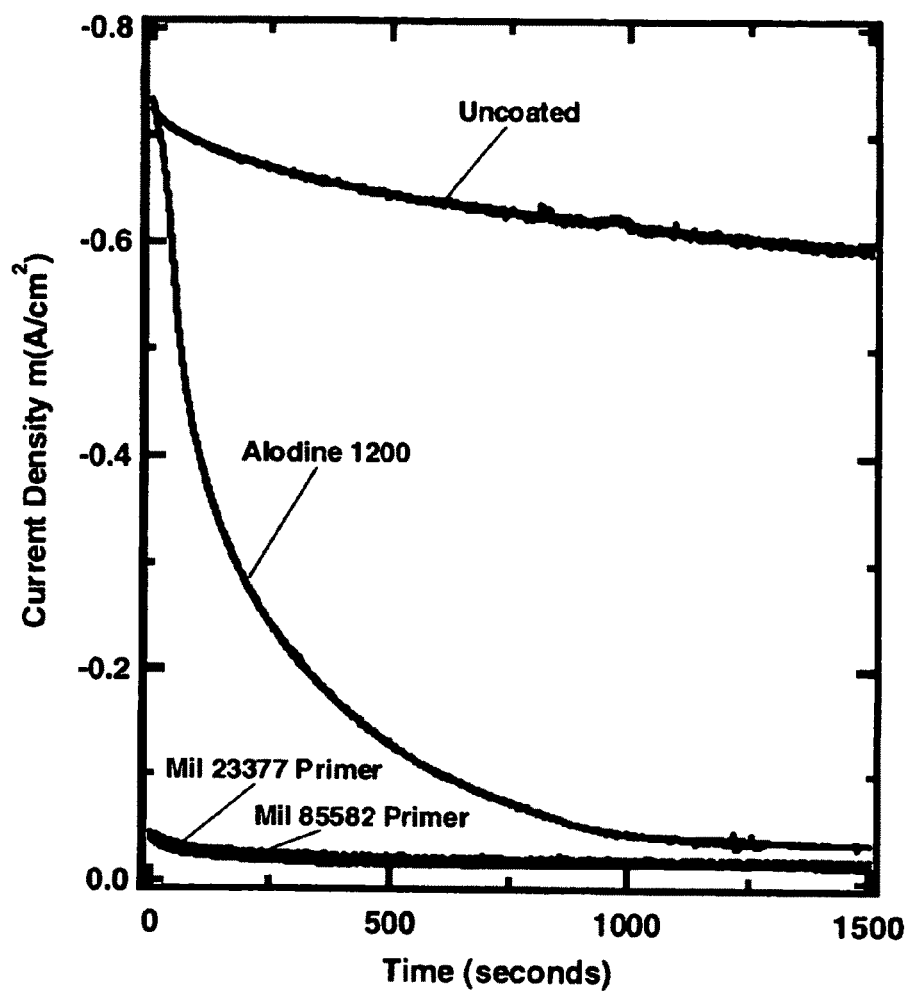
FIG. 4 shows plots of current density vs. time during evaluations, according to the present invention, of Aluminum 2024-T3 substrates, uncoated and coated with Alodine 1200, Mil Spec (Military Specification) 85582 primer or Mil Spec 23377 primer.

FIG. 4 shows plots of current density vs. time during evaluations, according to the present invention, of Aluminum 2024-T3 substrates, uncoated and coated with Alodine 1200, Mil Spec (Military Specification) 85582 primer or Mil Spec 23377 primer. Although the time required to reach a steady-state current plateau varies (as indicated in FIG. 4), experience with a wide range of coatings indicates that a steady-state current is generally attained within 1000 seconds.

Table 1 shows the oxygen reduction currents measured after 1000 seconds at −0.7 V for various coatings on Aluminum 2024-T3 substrates. Table 1 also lists values for the ratio of the oxygen reduction current for the uncoated substrate to that for the coated substrate. This ratio provides a figure of merit for the corrosion inhibiting activity of the coating (higher ratio indicates higher activity).

TABLE 1

Oxidation Reduction Currents Measured for Various Coatings

| Coating | Oxygen Reduction Current (mA/cm$^2$) | Uncoated/Coated Current Ratio |
|---|---|---|
| Uncoated | 0.62 | 1.0 |
| Mil Spec 85582 | 0.016 | 39 |
| Mil Spec 23377 | 0.020 | 31 |
| Alodine 1200 | 0.0445 | 14 |

We claim:

1. An apparatus for evaluating the corrosion inhibiting activity of a coating, comprising:
    a non-corroding rotating disk cathode comprising an oxygen reduction catalyst;
    an anode;
    an electrolytic solution;
    a means for applying a voltage between said cathode and said anode, wherein said cathode, said anode and the coating are in electrical contact with said electrolytic solution, and said cathode is positioned a predetermined distance of less than 1.0 mm from the coating surface; and
    a means for detecting corrosion inhibiting species released from said coating into said solution.

2. The apparatus of claim 1, further comprising a reference electrode in electrical contact with said electrolytic solution.

3. The apparatus of claim 2, wherein said means for applying a voltage between said cathode and said anode includes a potentiostat.

4. An apparatus for evaluating the corrosion inhibiting activity of a coating, comprising:
    a non-corroding rotating disk cathode comprising an oxygen reduction catalyst;
    an anode;
    a reference electrode;
    an electrolytic solution;
    a potentiostat for applying a potential to said cathode relative to said reference electrode, wherein said cathode, said anode and the coating are in electrical contact with said electrolytic solution, and said cathode is positioned a predetermined distance of less than 1.0 mm from the coating surface; and
    a means for detecting corrosion inhibiting species released from said coating into said solution.

5. The apparatus of claim 1, wherein said means for detecting corrosion inhibiting species released from said coating into said solution comprises a means for monitoring the oxygen reduction current at said cathode.

6. The apparatus of claim 5, further comprising a reference electrode in electrical contact with said electrolytic solution, wherein said means for monitoring the oxygen reduction current at said cathode comprises applying a potential to said cathode relative to said reference electrode such that diffusion limited oxygen reduction occurs at said cathode and corrosion inhibiting species released from said coating are transported to said cathode surface and suppress said oxygen reduction current.

7. The apparatus of claim 4, wherein said means for detecting corrosion inhibiting species released from said coating into said solution comprises a means for monitoring the oxygen reduction current at said cathode.

8. The apparatus of claim 7, wherein said means for monitoring the oxygen reduction current at said cathode comprises applying a potential to said cathode relative to said reference electrode such that diffusion limited oxygen reduction occurs at said cathode and corrosion inhibiting species released from said coating are transported to said cathode surface and suppress said oxygen reduction current.

* * * * *